US010143663B2

(12) United States Patent
Chami

(10) Patent No.: US 10,143,663 B2
(45) Date of Patent: *Dec. 4, 2018

(54) DETOXIFYING ANTIMICROBIAL MOLECULAR COMPLEX

(71) Applicant: ADNANE REMMAL, Fes (MA)

(72) Inventor: Ahmed Reda Chami, Casablanca (MA)

(73) Assignee: ADNANE REMMAL, Fes (MA)

(*) Notice: Subject to any disclaimer, the term of this patent is extended or adjusted under 35 U.S.C. 154(b) by 0 days.

This patent is subject to a terminal disclaimer.

(21) Appl. No.: 15/879,475

(22) Filed: Jan. 25, 2018

(65) Prior Publication Data

US 2018/0147158 A1    May 31, 2018

Related U.S. Application Data

(63) Continuation of application No. 14/758,284, filed as application No. PCT/MA2013/000054 on Dec. 31, 2013, now Pat. No. 9,901,550.

(30) Foreign Application Priority Data

Dec. 31, 2012    (MA) .......................... 35519

(51) Int. Cl.

| | | |
|---|---|---|
| *A61K 31/05* | (2006.01) |
| *A61K 47/02* | (2006.01) |
| *A23K 20/195* | (2016.01) |
| *A61K 9/14* | (2006.01) |
| *A01N 35/02* | (2006.01) |
| *A01N 31/16* | (2006.01) |
| *A01N 31/08* | (2006.01) |
| *A01N 31/06* | (2006.01) |
| *A01N 25/12* | (2006.01) |
| *A01N 25/08* | (2006.01) |
| *A23K 20/111* | (2016.01) |
| *A23K 20/10* | (2016.01) |
| *A23K 50/90* | (2016.01) |
| *A23K 50/80* | (2016.01) |
| *A23K 50/75* | (2016.01) |
| *A23K 50/50* | (2016.01) |
| *A23K 50/30* | (2016.01) |
| *A23K 50/20* | (2016.01) |
| *A23K 50/10* | (2016.01) |
| *A23K 20/28* | (2016.01) |
| *A61K 31/045* | (2006.01) |

(52) U.S. Cl.
CPC .............. *A61K 31/05* (2013.01); *A01N 25/08* (2013.01); *A01N 25/12* (2013.01); *A23K 20/10* (2016.05); *A23K 20/111* (2016.05); *A23K 20/195* (2016.05); *A23K 20/28* (2016.05); *A23K 50/10* (2016.05); *A23K 50/20* (2016.05); *A23K 50/30* (2016.05); *A23K 50/50* (2016.05); *A23K 50/75* (2016.05); *A23K 50/80* (2016.05); *A23K 50/90* (2016.05); *A61K 9/143* (2013.01); *A61K 31/045* (2013.01); *A61K 47/02* (2013.01); *Y02A 40/818* (2018.01)

(58) Field of Classification Search
CPC ...... A61K 31/05; A61K 9/143; A61K 31/045; A61K 47/02; A23K 20/195; A23K 20/28; A23K 50/10; A23K 50/20; A23K 50/30; A23K 50/50; A23K 50/75; A23K 50/80; A23K 50/90; A23K 20/10; A23K 20/111; A01N 25/08; A01N 25/12
USPC .......................................................... 514/731
See application file for complete search history.

(56) References Cited

U.S. PATENT DOCUMENTS

| 9,901,550 B2 * | 2/2018 | Chami ................. A61K 31/05 |
| 2011/0033576 A1 | 2/2011 | Yiannikouris et al. |
| 2013/0230431 A1 | 9/2013 | Mirowski |

FOREIGN PATENT DOCUMENTS

| EP | 1 132 009 | 9/2001 |
| EP | 2 481 413 | 8/2012 |
| GB | 984290 | 2/1965 |
| WO | WO 99/53772 | 10/1999 |
| WO | WO 2008/149232 | 12/2008 |

OTHER PUBLICATIONS

Brenes, A., et al., "Essential oils in poultry nutrition: Main effects and modes of action," *Animal Feed Science and Technology*, 2010, vol. 158, pp. 1-14.
Damiri, H., et al., "Effect of Different Sodium Bentonite Levels on Performance, Carcass Traits and Passage Rate of Broilers," *Pakistan Veterinary Journal*, 2012, vol. 32, No. 2, pp. 197-200.
Kéïta, S.M., et al., "Effect of various essential oils on *Callosobruchus maculatus* (F.) (Coleoptera: Bruchidae)," *Journal of Stored Products Research*, 2000, vol. 36, pp. 355-364.
Kéïta, S.M., et al., "Insecticidal effects of *Thuja occidentalis* (Cupressaceae) essential oil on *Callosobruchus maculatus* [Coleoptera: Bruchidae]," *Canadian Journal of Plant Science*, Jan. 1, 2000, vol. 81, pp. 173-177.
Nguemtchouin, M.M.G., et al., "Insecticidal formulation based on *Xylopia aethiopica* essential oil and kaolinite clay for maize production," *Crop Protection*, 2010, vol. 29, pp. 985-991.
Nguemtchouin, M.M.G., et al., "Ocimum gratissimum essential oil and modified montmorillonite clay, a means of controlling insect pests in stored products," *Journal of Stored Products Research*, Jan. 2013, vol. 52, pp. 57-62.

\* cited by examiner

*Primary Examiner* — Kristin A Vajda
(74) *Attorney, Agent, or Firm* — Saliwanchik, Lloyd & Eisenschenk

(57) ABSTRACT

The invention relates to a food additive which includes at least one clay interspersed with volatile antimicrobial agents. Such an additive can be added to the feed of certain animals, in particular poultry and ruminants, in order to act as a growth promoter and to reduce the risks of infection, as well as the risks of intoxication by mycotoxins.

17 Claims, No Drawings

DETOXIFYING ANTIMICROBIAL MOLECULAR COMPLEX

CROSS-REFERENCE TO RELATED APPLICATIONS

This application is a continuation of U.S. application Ser. No. 14/758,284, filed Jun. 29, 2015, which is the U.S. national stage application of International Patent Application No. PCT/MA2013/000054, filed Dec. 31, 2013.

The present invention relates to an additive for a veterinary feed, a composition containing this additive as well as the method for manufacturing this composition and the use of this composition as an additive with multiple actions: growth promoter action, plus protective action against parasitic diseases, plus adsorbing action of mycotoxins, plus immunostimulating and intestinal and hepatobiliary protective action.

Pathologies which affect animals are generally multifactorial phenomena in which several elements are involved: bacteria, viruses, fungi, parasites, immunodeficiency, metabolism, physiology, zootechnical environment, dietary deficiencies, toxins and others. The breeder generally has various products which each treat one or two factors alone. He is therefore forced to compose cocktails from these products. This has the consequence of risk of inadequacy of treatment by excess or lack, generating diverse losses. The most used administration route for these treatments is the oral route by addition in the feed or drinking water.

Cattle feed inter alia contains antibiotics used as growth promoters and antiparasitic agents like a preventive treatment for coccidiosis or histomoniasis and other parasitic diseases. These chemotherapeutic agents are questioned in several problems of animal health and public health for their toxicity, the residues which they may generate in food products of animal origin and their involvement in the emergence of resistance to infectious agents (Cháfer-Pericás et al., Food Control 22 (2011) 993-999).

It is for all these reasons that these agents were banned in several regions of the world. IP/05/1687, Brussels, Dec. 22, 2005.

Cattle feed also contains non-negligible concentrations of mycotoxins originating from mold which contaminate the cereals contained in the cattle feed. These mycotoxins have deleterious effects on animal health and their residues in foods of animal origin are deleterious for the health of the consumer (Wayne and Bryden, Animal Feed Science and Technology 173 (2012) 134-158).

In this context, the cattle feed manufacturers and breeders confronted with problems of delayed growth and parasitic diseases are forced to find alternatives for replacing the antibiotics used as growth promoters and the antiparasitic agents which have been banned as additives in the feed. They also have to find additives for combating the negative effects related to the presence of mold which produces mycotoxins and the mycotoxins themselves (Placinta et al., A review of worldwide contamination of cereal grains and animal feed with *Fusarium* mycotoxins, Animal Feed Science and Technology, Volume 78, Issue 1, Pages 21-37, 31 Mar. 1999).

In order to prevent these mycotoxins from passing into the bloodstream, several means are used. The most used means is the use of adsorbents such as hydrated sodium calcium aluminosilicate (HSCAS), activated coal, yeast walls, phyllosilicates, cholestyramine, and lactic bacteria (Phillips, Clement and Park, 1994, Approaches to reduction of aflatoxins in foods and feeds, in D. L. Eaton & J. D. Groopman, eds., *The toxicology of aflatoxins—human health, veterinary and agricultural significance*, p. 383, San Diego, Calif., United States, Academic Press).

Clays activated by the addition of acids and by heating are among those adsorbents (EP 1 333 919 B 1, Use of activated layered silicates for the adsorption of mycotoxins). However, the activation processes are very complicated and very expensive, which has a negative repercussion on the quality and reproducibility of the capability of adsorbing mycotoxins and makes the price of clays too expensive, especially when this is cattle feed.

Another problem related to activated clays consists of the fact that these clays may act as chelators of vitamins and reduce the amount of vitamins available for the animal. This may generate problems of vitamin deficiencies.

Among the alternatives used for replacing the antibiotics and antiparasitic agents, one finds essential oils and their majority compounds such as thymol, carvacrol, cinnamaldehyde, eugenol and others (Alleman et al., The use of essential oils in poultry feed, INRA Productions Animales, 2013, No. 1; Bento et al., Essential oils and their use in animal feeds for monogastric animals, Veterinarni Medicina, 58, 2013 (9): 449-458; Brenes and Roura, Animal Feed Science and Technology, 158 (2010) 1-14).

However, these substances are volatile and therefore unstable in the feed. This instability is at the origin of a significant loss of essential oils during the manufacturing of the feed. This forces cattle feed manufacturers to add large amounts of essential oils in excess so that the feed, once it is manufactured, still contains the required amount of essential oils, or to use complicated and expensive stabilization methods such as micro-encapsulation (de Barros Fernandes et al., Gum arabic/starch/maltodextrin/inulin as wall materials on the microencapsulation of rosemary essential oil, Carbohydrate Polymers 101 (2014) 524-532).

This instability is also at the origin of the short period of validity of the sought actions in cattle feed after manufacture. This has a negative repercussion on the quality of the feed containing the essential oils as an additive and increases the price of the additive, which reduces its competitiveness with antibiotics, antiparasitic agents and other alternatives.

The object of the present invention therefore consists of inventing a stable composition containing compounds having an antibiotic (antibacterial) and antiparasitic activity, an anti-fungal activity capable of inhibiting the growth of fungi secreting mycotoxins and at the same time the capability of adsorbing mycotoxins. Another object of the invention consists of selecting, from among substances having the activities mentioned above, those which also have an intestinal and hepatobiliary protective and immunostimulating activity.

Thus, against pathologies which are multifactorial phenomena affecting animal health, the invention proposes a solution with multiple actions.

The composition which is the object of the present invention and intended to achieve the aforementioned goal results from complexation by interspersing volatile molecules such as thymol, cresol, carvacrol, menthol, eugenol, and cinnamaldehyde, having an antibacterial, antiparasitic, antifungal and intestinal, hepatobiliary protective and immunostimulating activity with clays. The clay has at the same time the action of a stabilizer excipient of the composition, the action of adsorbing mycotoxins and the action of intestinal protectors.

The expression "molecular complex" refers to any composition obtained by mixing essential oils or one of their volatile compounds with any edible clay, the molecules of which are capable of interacting with these essential oils and their volatile compounds.

The expression "essential oils" refers to any extract obtained from aromatic plants by one of the known extraction methods allowing them to be extracted.

The expression "volatile compounds of the essential oils" refers to any volatile molecule obtained by purification from essential oils or from another natural source or else by identical chemical synthesis, as well as their derivatives and isomers.

The expression "edible clay" refers to any natural or synthetic mineral substance having a molecular structure identical or similar to that of edible clays commonly used in the agrifood and pharmaceutical field.

The expression "interspersed clay" refers to any situation where interspersing molecules come into interaction with clay molecules by being inserted into the interfoliar spaces of clay, this interspersion being expressed by an increase in the interfoliar distance.

The expression "antimicrobial activity" refers to any inhibitory or destructive action on microbial germs of a bacterial, fungal, parasitic or viral nature.

The expression "intestinal and hepatobiliary protector" refers to any action allowing to preserve the physical and physiological integrity of the intestine and to stimulate the hepatic function so as to increase its detoxification activity.

The expression "immunostimulating" refers to any activity allowing to reinforce natural or acquired defenses of the organism.

The expression "adsorbing toxins" refers to any activity allowing the binding of the toxins at the intestinal level in order to prevent their absorption into the bloodstream.

Animal husbandry is confronted with a multitude of risk factors of the zootechnical, infectious, sanitary, hygienic, immune, physiological and feed order which promote the occurrence of pathologies which only one of these factors could not cause. It is for this reason that scientists agree on the idea that the occurrence of any disease is a multifactorial phenomenon (Sjaak de Wit, Practical epidemiology of poultry disease and multifactorial conditions, Poultry Diseases (Sixth Edition), 2008, Pages 492-509).

Hence the benefit of studying the impact of each factor separately and of providing a curative or preventive remedy to each of them in order to prevent the outbreak of the disease or to attenuate the damages which it causes. The multitude of remedies poses problems of cost, dosage of each remedy and many other problems which complicate the work of the breeder.

In order to overcome the problem of the use of antibiotics and antiparasitic agents of chemotherapy banned by regulations and the problem of multiple remedies, the object of the present invention is therefore a stable composition comprising a molecular complex containing natural molecules having multiple pharmacological, antimicrobial, immunostimulating, cholagogue, and carminative activities, such as thymol, cresol, carvacrol, menthol, eugenol, cinnamaldehyde, or any component containing them separately or mixed, as well as the isomers, derivatives and mixtures thereof. These volatile molecules are bound and stabilized by interspersion into the inferfoliar space of clays having properties for adsorption of toxins, intestinal protectors, and hydrating properties such as stevensite, bentonite, kaolinite, smectite, illite, chlorite, montmorillonite, laponite, beidellite, nontronite, saponite, sauconite, hectorite, halloysite, vermiculite, or sepiolite or their natural or caused interlayered mixtures.

In a particular embodiment, the composition may comprise said volatile antimicrobial agents which are antiseptic aromatic alcohols selected from thymol, cresol, carvacrol, menthol, eugenol, cinnamaldehyde, or any component containing them separately or mixed as well as the isomers, derivatives and mixtures thereof. These agents are interspersed in edible clays selected from stevensite, bentonite, kaolinite, smectite, illite, chlorite, montmorillonite, laponite, beidellite, nontronite, saponite, sauconite, hectorite, halloysite, vermiculite, or sepiolite or their either natural or caused interlayered mixtures.

Said volatile antimicrobial agent is present in said composition in a weight ratio ranging from 0.005 to 0.33 compared to said edible clay.

The method for manufacturing said composition comprises the following steps:

i) Said volatile antimicrobial agent is put into solution in an organic or mineral solvent in order to obtain the antimicrobial solution.

ii) Said thereby obtained antimicrobial solution is mixed with said edible clay as a powder or pellets under stirring and temperature conditions, giving the possibility of obtaining a homogeneous and stable composition formed by a molecular complex containing said edible clay interspersed by said volatile antimicrobial agent.

In a particular embodiment, this manufacturing method may be detailed as follows:

An amount of volatile antimicrobial agent is gradually put into solution in an amount of vegetable or mineral oil, representing 1 to 20% of the amount of volatile antimicrobial agent, stirred and heated to a temperature ranging from 30 to 80° C. in order to obtain a homogeneous and limpid liquid solution, a so-called antimicrobial solution.

An amount of the antimicrobial solution is gradually included by mixing in an amount of said powdered edible clay, representing at least three times the amount of antimicrobial solution, in order to obtain a sievable powder.

The obtained sievable powder is calibrated by sieving in order to obtain the desired grain size.

In a particular embodiment, the volatile antimicrobial agent may be thymol alone or mixed with one or several other volatile antimicrobial agents such as cresol, eugenol, carvacrol, cineol, menthol or cinnamaldehyde or any essential oil containing them separately or mixed and the edible clay may be stevensite or bentonite or their mixture or the mixture of substances containing them.

In a preferred embodiment, the preparations as detailed above will be intended to be diluted in cattle feed for administration to an animal. This dilution may be carried out in a ratio ranging from 50 grams of preparation per metric ton of feed to 10 kilograms of preparation per metric ton of feed.

In a further preferred embodiment, said preparation, before dilution in the feed, may contain the volatile antimicrobial agent at a weight ratio ranging from 0.1 to 0.33 compared to the edible clay, preferentially in a weight ratio from 0.15 to 0.2 compared to clay.

One object of the present invention is the use of said composition as a feed additive for animals, added to the feed and taken via an oral route.

In every case, the use of said compositions as feed additives is intended to exert a multitude of actions emanating from the properties of the substances which they contain, e.g.:

the growth-promoting activity due to the antiseptic properties of the volatile antiseptic agents capable of reducing pathogenic or commensal intestinal flora;

the antiparasitic, anticoccidian and antihistomoniasis activity, in particular due to the antiparasitic activity of the volatile antimicrobial agents;

the antifungal activity due to the antifungal activity of the volatile antimicrobial agents, giving the possibility of inhibiting the fungi responsible for production of mycotoxins;

the mycotoxin adsorption activity due to the chelating properties of clays;

the cholagogue activity due to the pharmacological properties of the volatile antimicrobial agents;

the immunostimulating activity due to the pharmacological properties of the volatile antimicrobial agents; and the protective intestinal activity due both to the intestinal bandage properties of the clay and the antiseptic intestinal properties of the volatile antimicrobial agents.

In every case, the use of said compositions as feed additives intended to exert a multitude of favorable actions on the animal's body has the consequence of preserving intestinal, hepatobiliary and immune integrity with positive repercussions on preserving the general health of the animals receiving said compositions as feed additives.

The examples which follow are intended to illustrate certain aspects of the invention without, however, being limiting.

On the one hand, the inventor proceeded with experiments with different types of volatile antimicrobial agents and different types of clays. The results gave the possibility of showing a displacement of the diffraction x-ray peaks of the characteristic molecules of the clays tested, i.e., stevensite and bentonite, in a direction which shows an increase in the interfoliar distance of interspersed clays by volatile antimicrobial agents as compared with clays before interspersion. This justifies and explains the perfectly stable bond of the volatile antimicrobial agents on the clays when they are mixed according to the method that is the object of the invention. On the other hand, the inventor tested the efficiency of the composition with particularly effective doses and ratios of the composition under in vitro and in vivo conditions.

EXAMPLE 1

X-Ray Diffraction Test

Preparations of a final weight of 1,000 grams were made with 150 grams of thymol put into solution according to the method of the invention with 20 milliliters of table oil at a temperature of 60° C. The antiseptic solution obtained thereby was mixed with 830 grams of Moroccan ghassoul, 830 grams of Moroccan bentonite, or 830 grams of a 50%/50% ghassoul/bentonite mixture (preparation a).

Control compositions were prepared:

Preparation b: The same pure clays without any additive.

Preparation c: The same clays with 20 ml of table oil alone.

Preparation d: The same clays with thymol alone as a crystallized powder.

Preparation e: The same clays with liquefied thymol by heating to 60° C. without any vegetable oil.

Preparations a, b and c were subjected to an x-ray diffraction test according to the usual standards for treating clays in this analytical method.

The results obtained show a displacement of the specific peaks of bentonite and stevensite in the spectrum, in a surprising way in the case of the preparations according to the method of the invention (preparation a) as compared with the controls of pure clays (preparation b) and clays having been mixed with table oil alone (preparation c) (results in Table 1). At the same time, the results show that for preparation d containing thymol as a crystallized powder mixed with clay, the obtained powder is heterogeneous and the obtained x-ray diffraction spectrum was not able to be utilized. For preparation e, in which thymol was liquified by heating and mixed with clay without any vegetable oil, it is seen that thymol recrystallizes and forms hard lumps. The mixture obtained thereby is heterogeneous and cannot meet the criteria for which the invention was elaborated.

This shows on the one hand that the manufacturing method used in the invention actually gives the possibility of ending up with interspersion of thymol in the interfoliar spaces of the clays, which leads to a stable and homogeneous dispersion of thymol in clay and an increase in the distance of the interfoliar spaces of the clays, therefore improving hydrophobicity and the capability of the clays of adsorbing the toxins.

These results show on the other hand that the mixtures with thymol and clay by obvious methods using crystallized thymol or liquified thymol by heating do not end up with the result expected by the invention.

TABLE 1

Interfoliar distance of the clays according to preparation modes a, b and c

| | Clays | | | | | |
|---|---|---|---|---|---|---|
| | Bentonite | | | Stevensite | | |
| | Crude (prep. b) | With table oil (prep. c) | With table oil and essential oil (prep. a) | Crude (prep. b) | With table oil (prep. c) | With table oil and essential oil (prep. a) |
| Distance between sheets (in angstroms) | 15.23 | 15.23 | 15.69 | 15.75 | 16.15 | 16.51 |

EXAMPLE 2

In Vivo Test

Batches of 25 young broilers and 12 turkey poults were fed with a feed containing the preparation of the invention in an amount of 100 grams, 500 grams, 1 kilogram or 2 kilograms per metric ton of feed. Control batches of the same size were fed with a feed not containing any antibiotic or antiparasitic agents. Other control batches of the same size were fed with a feed containing Flavomycin in an amount of 200 grams per metric ton of feed and Salinomycin in an amount of 70 grams per metric ton of feed for the broilers and 100 grams per metric ton of monensin for the turkey poults. During five weeks of treatment, feces samples of each subject in each batch were analyzed by microscopy and by suitable microbiological analysis for evaluating the numbers of bacteria, yeast, fungi and oocytes of protozoa, in particular of the species *Eimeria*. sp., involved in coccidiosis in chickens and turkeys. At the end of the five weeks of the experiment, the subjects were sacrificed and autopsies were carried out by professional veterinarians, specialists in avian pathology. The goal of the autopsies was to evaluate the lesional scores of the intestine and the integrity condition of the liver, kidneys, lungs, spleen and intestine.

The results obtained show highly significant reductions in the numbers of bacteria, yeasts, fungi and oocytes in the batches having received the preparation of the invention in their feed at doses of 1 kilogram per metric ton and 2 kilograms per metric ton as compared with control batches having received a neutral feed. The batches having received the preparation of the invention in their feed at doses of 100 grams and 500 grams per metric ton of feed did not have any significant difference as compared with the control. The batches having received the antibiotic and the antiparasitic agent in their feed have a visible but non-significant reduction as compared with the controls. However, the numbers of bacteria, yeasts, fungi and oocytes in batches having received the preparation of the invention at the doses of 1 kilogram and 2 kilograms per metric ton of feed is significantly less than the number of bacteria, yeasts, fungi and oocytes recorded in the batches having received the antibiotic and the antiparasitic agent in the feed. These results show that the preparation according to the invention used as an additive in chicken and turkey feed has multiple activities like promoting growth (reduction in the intestinal flora), as an antiparasitic (anticoccidian) agent and as an antifungal agent significantly superior to the antibiotics and antiparasitic agents used in this test. The results of the autopsies also show that the intestinal lesion, kidney, lung, spleen and liver congestion scores are significantly lower in the batches having received the feed containing the preparation of the invention as compared with the batches having received the neutral feed or the feed containing the antibiotic and the antiparasitic agent. These results again show that the preparation of the invention used as an additive in chicken and turkey feed has activities protecting intestinal integrity, hepatobiliary protective activities, and activities purifying the lungs and kidneys and protecting the spleen. These results confirm that the preparation of the invention represents a solution with multiple activities for combating pathologies of chickens and turkeys which are multifactorial diseases.

Batches of 25 chicks of one day of age were fed for 5 weeks on average with respectively:
batch 1: a white "broiler" feed which contains neither antibiotics nor antiparasitic agents;
batch 2: a feed containing a growth factor antibiotic, "Flavomycin," in an amount of 200 milligrams per kilogram of feed and an antiparasitic agent, "Salynomycin," in an amount of 70 milligrams per kilogram;
batch 3: a feed containing the preparation of the invention in the feed at a proportion of 100 grams per metric ton of feed;
batch 4: a feed containing the preparation of the invention in the feed at a proportion of 500 grams per metric ton of feed;
batch 5: a feed containing the preparation of the invention in the feed at a proportion of 1 kg per metric ton of feed; and
batch 6: a feed containing the preparation of the invention in the feed at a proportion of 2 kg per metric ton of feed.

TABLE 2

Zootechnical and microbiological results of the broiler in vivo test

| | Mortality rate | Consumption index | Body weight (g) | Bacterial load (CFU/g of faeces) | Fungal load (CFU/g of faeces |
|---|---|---|---|---|---|
| Batch 1 | 0% | 2.3 | 105 ± 8.6 | $1 \cdot 10^{10} \pm 0.3$ | $8.6 \cdot 10^9 \pm 3.7$ |
| Batch 2 | 0% | 2.2 | 110 ± 6.4 | $4.9 \cdot 10^9 \pm 2.1$ | $1.6 \cdot 10^9 \pm 0.3$ |
| Batch 3 | 0% | 2.2 | 113 ± 3.4 | $4.5 \cdot 10^9 \pm 3.2$ | $5.7 \cdot 10^8 \pm 1.2$ |
| Batch 4 | 0% | 2.1 | 121 ± 4.5 | $3.2 \cdot 10^8 \pm 4.1$ | $1.3 \cdot 10^8 \pm 0.3$ |
| Batch 5 | 0% | 1.9 | 138 ± 6.6 | $7.3 \cdot 10^7 \pm 5.2$ | $8.6 \cdot 10^7 \pm 1.5$ |
| Batch 6 | 0% | 1.8 | 157 ± 2.2 | $2 \cdot 10^7 \pm 1.70$ | $5 \cdot 10^7 \pm 1.1$ |

The in vivo test for turkeys gave similar results to those obtained in the broiler chicken in vivo test.

EXAMPLE 3

Field Tests

Field tests were carried out on a farm raising chicken broilers and a farm raising turkey broilers. In these tests, two batches of 13,500 chicks each received the preparation of the invention at the dose of two kilograms per metric ton of feed during the whole duration of the tape (40 days for chickens and 13 weeks for turkeys). Two other batches of 13,500 chicks each received the preparation of the invention at the dose of 1 kilogram per metric ton of feed and two other batches of 13,500 chicks each received a feed containing the antibiotic Flavomycin at 200 grams per metric ton of feed and the antiparasitic agent Salynomycin at 70 grams per metric ton of feed for chickens and monensin for turkeys. At the end of the strip, the zootechnical performances and the lesion scores were measured for each batch.

The Results Show:
Mortality: The percentage of dead chickens and turkeys during the raising cycle was 2.9% for chickens and 2.5% for turkeys for the batches having received 1 kilogram or 2 kilograms of preparation of the invention per metric ton of feed. For the batches having received the antibiotic and the antiparasitic agent in the feed, the mortality was 5.2% for turkeys and 5.9% for chickens.

Average weight: The average weight of both batches having received 1 kilogram or 2 kilograms per metric ton of feed of the preparation of the invention is 2.3 kg per subject in chickens and 12.8 kg in turkeys; that of the two batches having received the antibiotic and the antiparasitic agent was 2.135 kg in chickens and 11.9 kg in turkeys.

Consumption index: The consumption index for the batches having received two kilograms of the preparation of the invention per metric ton of feed was 1.68, that of the batches having received one kilogram of the preparation per metric ton of feed was 1.82, and that of the two batches having received the antibiotic and the antiparasitic agent was on the order of 1.98.

The titers of the antibodies related to the vaccines used: The inhibition titer of hemagglutination as compared with the antibodies of the viruses of Newcastle's disease the batches having received the preparation in an amount of two kilograms and one kilogram per metric ton of feed was 64, 64, 64, 32 respectively and, for the two batches having received the antibiotic and the anti-coccidian agent, were 16 and 16.

The lesional score of the intestine: The lesional scores of the intestine were lowest (1.22) for the batches having received the preparation of the invention in an amount of 2 kg and 1 kg while the scores for the batches having received the antibiotic and the anti-coccidian agent were on the order of 2.74 and 3.13.

The score of the integrity of the organs: The aspect of the organs (liver, spleen, lungs, muscles and bones) were clearly more healthy (not showing any sign of congestion) for the batches having received the preparation of the invention in an amount of 2 kg and 1 kg per metric ton of feed, while congestion signs visible to the naked eye were ascertained in the majority of the autopsies in both batches having received the antibiotic and the antiparasitic agent.

These results surprisingly show that the preparation of the invention exerts the multiple activities for which it was designed even under intensive raising conditions in the field.

EXAMPLE 4

Inhibition and Adsorption of Mycotoxins in Feed and Corn

Samples of corn and composed feed were treated with variable amounts of the preparation of the invention in the proportions of 2 kg, 4 kg and 6 kg per metric ton of feed. These samples were hermetically packaged and incubated at a temperature of 27.5° C. 50 gram aliquots were taken after four weeks for dosage of the mycotoxins; the results show that the corn samples having been treated by the preparation of the invention had significantly lower levels of DON (deoxynivalenol), ZON (Zearalenone) and ochratoxin than the control sample. This inhibition and adsorption effect on mycotoxins is increased according to the dose used of the preparation of the invention. A similar result was obtained for the composed feed sample treated by the preparation of the invention with respect to the untreated sample for mycotoxins, ochratoxin (ZON) and aflatoxin.

These results show that the preparation of the invention also has the capability of protecting feed and corn from mycotoxins which represent a significant risk factor promoting the outbreak of diseases and causing, in acute cases, mortal intoxication of animals.

TABLE 3

Percentage of reduction of the mycotoxins in corn treated with the preparation of the invention as compared with the untreated control

| | Preparation | | |
|---|---|---|---|
| Mycotoxins | 0.2 g/100 g of corn | 0.4 g/100 g of corn | 0.6 g/100 g of corn |
| Zearalenone | 56% | 59% | 61% |
| DON | 63% | 73% | 75% |
| Ochratoxin | 13% | 22% | 27% |

TABLE 4

Reduction percentage of the mycotoxins in the treated composed feed with respect to the untreated control.

| | Preparation | | |
|---|---|---|---|
| Mycotoxins | 0.2 g/100 g of feed | 0.4 g/100 g of feed | 0.6 g/100 g of feed |
| Zearalenone | 35% | 63% | 94% |
| Aflatoxin | 74.35% | 86% | 89% |

I claim:

1. A composition combining both antimicrobial and toxin-adsorption activities, characterized in that it is formed by a molecular complex comprising an edible clay interspersed by a volatile antimicrobial agent, characterized in that said edible clay is a mixture of Ghassoul and bentonite.

2. The composition according to claim 1, characterized in that said volatile antimicrobial agent is an antiseptic aromatic alcohol selected from thymol, cresol, carvacrol, eugenol, menthol, cinnamaldehyde or mixtures or isomers thereof.

3. The composition according to claim 1, characterized in that said volatile antimicrobial agent is formed by a mixture of two or more natural or synthetic antimicrobial agents.

4. The composition according to claim 1, characterized in that said mixture of Ghassoul and bentonite contains at least 5% by weight Ghassoul from Morocco.

5. The composition according to claim 1, characterized in that said volatile antimicrobial agent is present in a mass ratio from 0.005 to 0.33 based on said edible clay.

6. A method for manufacturing a composition comprising an edible clay and a volatile antimicrobial agent comprising:
   i) adding said volatile antimicrobial agent into solution with an organic or mineral solvent in order to obtain an antimicrobial solution; and
   ii) mixing said antimicrobial solution with said edible clay as a powder or pellets under stirring and temperature conditions to obtain a homogenous and stable composition formed by a molecular complex containing said edible clay interspersed by said volatile antimicrobial agent, characterized in that said edible clay is a mixture of Ghassoul and bentonite.

7. The manufacturing method according to claim 6, characterized in that said volatile antimicrobial agent is selected from thymol, cresol, carvacrol, menthol, eugenol, cinnamaldehyde, or mixtures or isomers thereof, said organic or mineral solvent is a vegetable oil.

8. The manufacturing method according to claim 6 wherein:
   crystallized thymol is gradually put into solution in a volume of vegetable oil heated to a temperature allowing it to melt so as to obtain a homogeneous and limpid liquid composition (an antimicrobial solution);
   mixing said antimicrobial solution with an amount of said edible clay as a powder capable of absorbing it in order to obtain a molecular complex as a homogenous and stable powder; and
   subjecting said powder to a calibration or sieving operation to obtain the desired grain size.

9. The manufacturing method according to claim 6, characterized in that the volatile antimicrobial agent is a mixture of thymol and cresol.

10. The manufacturing method according to claim 6, characterized in that the volatile antimicrobial agent is a mixture of thymol, cresol and menthol.

11. A method of reducing or suppressing the development of pathogenic or toxinogenic germs in an animal comprising administering a composition according to claim 1 to an animal or its surroundings.

12. The method according to claim 11, wherein said composition is administered to said animal in a feed containing said composition.

13. The method according to claim 11, wherein said composition is added to feed, drinking water, litter, walls of the animal enclosure, barn area, rearing equipment or the vehicles transporting the animal.

14. The method according to claim 11, wherein said animal is a mammal, fish, bee or poultry.

15. The method according to claim 14, wherein said mammal is a bovine animal, ovine animal, rabbit, pig, caprine animal or equine animal.

16. The method according to claim 14, wherein said poultry are selected from chicken broilers, laying hens, breeding roosters and hens, guinea fowl, turkeys, quail, ducks, geese and pigeons.

17. The method according to claim 11, said method reducing or suppressing development of bacteria, fungi, parasites, bacteriotoxins and mycotoxins in the animal.

\* \* \* \* \*